United States Patent
Berndt (12)

(10) Patent No.: US 6,468,803 B1
(45) Date of Patent: Oct. 22, 2002

(54) METHOD FOR CALIBRATING A SAMPLE ANALYZER

(75) Inventor: Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/865,935

(22) Filed: May 25, 2001

(51) Int. Cl.[7] .................................................. G01N 21/64
(52) U.S. Cl. ........................... 436/63; 436/70; 436/165; 436/172; 356/72; 356/73
(58) Field of Search ................................ 436/8, 63, 70, 436/164, 165, 172; 356/72, 73, 440, 244, 246

(56) References Cited

U.S. PATENT DOCUMENTS

| | | | | |
|---|---|---|---|---|
| 3,977,995 A | * | 8/1976 | Louderback et al. | 356/39 |
| 5,427,959 A | * | 6/1995 | Nishimura et al. | 356/244 |
| 5,547,849 A | * | 8/1996 | Baer et al. | 435/287.2 |
| 5,898,487 A | * | 4/1999 | Hage | 356/39 |
| 6,064,474 A | * | 5/2000 | Lee et al. | 356/39 |
| 6,127,184 A | * | 10/2000 | Wardlaw | 356/244 |
| 6,259,524 B1 | * | 7/2001 | Hofstraat et al. | 356/243.4 |

* cited by examiner

*Primary Examiner*—Jeffrey Snay
(74) *Attorney, Agent, or Firm*—Bruce S. Weintraub, Esq.

(57) ABSTRACT

The present invention relates to the field of quantitative microspectroscopy, and in particular to a method for calibrating a sample analyzer, which is preferably a disposable sample analyzer.

43 Claims, 6 Drawing Sheets

METHOD FOR CALIBRATING A SAMPLE ANALYZER

FIELD OF THE INVENTION

The present invention relates to the field of quantitative microspectroscopy, and in particular to a method for calibrating a sample analyzer which is preferably a disposable sample analyzer.

BACKGROUND OF THE INVENTION

The determination of such blood parameters as the Hematocrit ("HCT"), the Volume of single Red Blood Cells ("RCV"), the Mean Cell Volume ("MCV") and the Red Cell Distribution Width ("RDW") are of eminent clinical interest. Usually, systems based on electrical impedance measurement (Coulter Counter) or based on light scattering (Flow Cytometer) are employed (see. e.g., J. B. Henry, "Clinical diagnosis and management by laboratory methods", W. B. Saunders Company, Philadelphia, 1996, pp. 548 ff. or D. H. Tycko, M. H. Metz, E. A. Epstein, A. Grinbaum, "Flowcytometric light scattering measurement of red blood cell volume and hemoglobin concentration", Applied Optics 24 (1985), 1355–1365). Impedance counters are complex and expensive instruments that require very careful adjustment and control of instrument and sample parameters. A major disadvantage of flow cytometers is the fact that the parameters of light scattering depend not only on cell volume, but also on the cell's shape.

In 1983, Gray, Hoffman and Hansen proposed a new optical method for determining the volume of cells in a flow cytometer (M. L. Gray, R. A. Hoffman, W. P. Hansen, "A new method for cell volume measurement based on volume exclusion of a fluorescent dye", Cytometry 3 (1983), 428–432). In this method, the cells are suspended in a fluorescent dye, which is unable to penetrate the cell membrane. The level of fluorescence which is produced when a narrow stream of the cell suspension is excited by a focused laser beam will remain constant until a cell arrives in the illuminated region thereby causing a decrease in fluorescence intensity which is directly proportional to the cell's volume. In a flow cytometer, a single cell is passing through the laser-illuminated spot within approximately 10 □s. Due to this short data acquisition time interval, the electronic detection bandwidth has to be relatively large, which results in a poor signal-to-noise ratio and in a low precision for the volume determination.

The available data acquisition time can be significantly increased by suspending the cells in a stationary sample and applying digital imaging fluorescence microscopy (see P. L. Becker, F. S. Fay, "Cell-volume measurement using the digital imaging fluorescence microscope", Biophysical Journal 49 (1986), A465). In the digital fluorescence microscopy approach, a calibration procedure is required in order to determine the cell volume. Recktenwald and co-workers have introduced a method where the calibration is performed by means of optical transparent and non-fluorescent microspheres that are suspended together with the cells (D. Recktenwald, J. Phi-Wilson, B. Verwer, "Fluorescence quantitation using digital microscopy", Journal Physical Chemistry 97 (1993), 2868–2870). The volume of individual spheres is determined by measuring their projection area under the microscope and transforming this number into a volume, assuming an ideal spherical shape. The decrease in fluorescence intensity as a result of the spheres' volume that is being excluded from emitting fluorescence is used as the required calibration parameter. The advantage of this approach is given by the fact that the calibrating particles are located within the sample itself. In other words, a calibration is performed on the very same sample container, and no extra calibration sample is required.

The use of calibration spheres within a cell suspension is not without problems. First, the introduction of the spheres represents an additional step in the workflow. In systems that are designed for high throughput, this additional step would represent a disadvantage. Secondly, Recktenwald and co-workers observed a tendency of the fluorescent dye molecules to settle down on the sphere's surface, which causes an error. Third, if the optical index of refraction of the spheres does not match well with the liquid's index, then refraction-based artifacts in the measured fluorescence intensity occur at the edges of the spheres. And, finally, the use of microspheres can represent a problem, if e.g. a thin sample thickness in the order of a few micrometers or less is needed.

In order to overcome the problems in the prior art, it was suggested, in U.S. Pat. No. 6,127,184 to Wardlaw, to design a cuvette-like optical sample container for the cell suspension that has different optical pathlengths in different areas. In at least one area, the thickness of the liquid layer of un-diluted blood is so thin (2 to 7 microns) that monolayers of isolated RBCs are formed. In another region, the liquid layer is thicker (7 to 40 microns), and typical chain-like aggregates of RBCs ("Roleaux") are forming. The thick area is used to determine the HCT, and the thin area is used to determine the volume of single red blood cells (RCV). As in the prior art, the blood plasma is stained with a fluorescent dye that is not penetrating into the RBCs.

In a method and apparatus described in U.S. Pat. No. 6,127,184, the HCT of the whole blood sample is determined according to the equation $$HCT = \left[1 - \frac{B_a}{B_t}\right] * 100\% \tag{1}$$

In equation (1), $B_t$ is the fluorescence intensity emerging from an area of known size within a cell-free plasma region. $B_a$ is the fluorescence intensity emerging from another area of same size, but from a region comprising RBCs in Roleaux formation. In practice, $B_t$ is determined by measuring the fluorescence intensity in certain cell-free regions and by extrapolating to a larger size. Interestingly, no height measurement is required for the cuvette in order to determine the HCT.

The volume of single Red Blood Cells, RCV, can be determined using the equation $$RCV = \left[1 - \frac{B_{RBC}}{B_P}\right] * A * d \tag{2}$$

where, similar to equation (1), $B_P$ is the fluorescence intensity emerging from an area of known size, A, within a cell-free plasma region. $B_{RBC}$ is the fluorescence intensity emerging from another area of same size, but comprising a single RBC. In practice, $B_P$ is determined by measuring the fluorescence intensity in a cell-free region near a particular RBC, and by extrapolating to the full size, A. In contrast to the HCT determination, the absolute area, A, and the absolute height of the liquid layer, d, have to be known. One could also say that the absolute volume $$V = A * d \tag{3}$$

in which the single RBC is embedded, has to be known. The area, A, can be easily determined under the microscope. The determination of the height, d, near the RBC is a more complicated problem and is named "calibration".

U.S. Pat. No. 6,127,184 discloses some methods to "calibrate" the optical cuvette, i.e. to determine the height, d. In one option, a square-shaped capillary of known volume is integrated into the cuvette. By measuring the fluorescence intensity reemerging from this capillary one obtains a calibration parameter C=intensity/volume. Since the fluorescence intensity per unit area is assumed to be proportional to the height of the cuvette, the height at any location can then be determined via the reemerging fluorescence intensity. In another method, U.S. Pat. No. 6,127,184 discloses the utilization of a molded calibration standard such as a well of accurately controlled depth.

However, the integration of a square-shaped capillary of known volume, or the use of a well of accurately controlled depth are likely to increase the complexity and therefore the cost of the cuvette-like optical sample container.

Consequently, there still exists a need for a calibration method for sample analyzer disposables that would not require any integrated or molded calibration tools of high precision.

SUMMARY OF THE INVENTION

It is an objective of the present invention to provide a method for calibrating a sample analyzer, and preferably, a disposable sample analyzer, and in particular a calibration method for the RCV determination in blood samples that would be exact, but would not require molded calibration tools of high precision within the sample analyzer.

According to the present invention, the above objective is achieved by depositing a sample of biological fluid, and preferably, whole blood, into a chamber, such as for example, an optical cuvette having at least two areas of different thickness, whereby in a preferred embodiment the blood plasma contains a fluorescent dye that does not diffuse into the red blood cells. The sample is put into an optical scanning instrument such as a fluorescence microscope and is illuminated with excitation light so that the plasma emits fluorescence radiation, which is detected by the microscope's imaging photodetector. The fluorescent dye is selected so that neither the excitation light nor the emitted fluorescence light are absorbed significantly by the red blood cells.

A height value in the single-cell area of the optical cuvette is then determined by performing the following process steps of:

(a) measuring fluorescence intensity values in cell-free locations within a calibration area of sufficient height;
(b) extrapolating to the integrated fluorescence intensity, Ical, for a total calibration area of size, A, that could be expected under cell-free conditions;
(c) measuring fluorescence intensity values in cell-free locations within the single-cell area;
(d) extrapolating to the integrated fluorescence intensity, Isca, for a total area of size, A, that could be expected under cell-free conditions;
(e) determining an effective height, H, by using the equation:

$$H = \int_{-h/2}^{h/2} E(z) * D(z) \, dz \qquad (4)$$

where $$E(z) = \left[ \frac{\sin(u_{ex}(z)/4)}{u_{ex}(z)/4} \right]^2 \qquad (5)$$

where $$u_{ex}(z) = \frac{2 * \pi}{\lambda_{ex}} * (NA)^2 * z \qquad (6)$$

where $$D(z) = \left[ \frac{\sin(u_{em}(z)/4)}{u_{em}(z)/4} \right]^2 \qquad (7)$$

where $$u_{em}(z) = \frac{2 * \pi}{\lambda_{em}} * (NA)^2 * z \qquad (8)$$

and wherein NA is the numerical aperture of the microscope objective lens, $\lambda_{ex}$ is the excitation center-wavelength, $\lambda_{em}$ is the emission center-wavelength, and z is a position within the sample on an axis parallel to the microscope's imaging optics;

(f) calculating a quantity K with the equation:

$$K = \frac{I_{sca}}{I_{cal}} * H \qquad (9)$$

(g) determining an integration limit, d, that is a solution of the equation:

$$\int_{-d/2}^{d/2} E(z) * D(z) \, dz = K \qquad (10)$$

whereby d is equal to the unknown sample height (which is equal to the cuvette height) in the single-cell area that is to be determined.

DETAILED DESCRIPTION OF THE INVENTION

According to the method of the present invention, a sample of a biological fluid, such as preferably, blood, and more preferably undiluted blood that contains suspended red blood cells ("RBCs") is deposited into a chamber, such as, for example an optical cuvette having at least two areas of different thickness. Preferably, the cuvette is relatively thin and suitable to be positioned onto the sample stage of a fluorescence microscope, and, preferably, a fluorescence microscope in EPI configuration where the sample is illuminated through the objective lens. The invention can also be applied if a confocal microscope is used.

A fluorescent dye is added to, and evenly distributed within the liquid sample. The dye is selected so that it does not leak into the RBCs. In other words, only the blood plasma is stained with a fluorescent dye. The dye should absorb excitation light within a spectral region where the absorption within the RBCs is only weak. Since hemoglobin is the dominant absorber in RBCs, the excitation wavelength should preferably be longer than 600 nm. In a preferred embodiment, the dye TO-PRO-3 (sold, for example, by Molecular Probes, Inc., Eugene, Oreg.), that can be excited within a wavelength range around 640 nm can be utilized. Another preferred dye is TO-PRO-5 (also sold by Molecular Probes, Inc.), which also does not penetrate into the RBCs, and can be excited around 750 nm.

An "EPI configuration" is a common term used in fluorescence microscopy. It means that nearly parallel excitation light is directed towards the objective lens (usually downward). The oncoming excitation light is focused by the objective lens onto the sample, forming a small area of high illumination intensity. Fluorescence light, that is generated within that area of the sample, is collected by the very same objective lens and forms a parallel fluorescence beam going upwards. A parallel beam is formed because the sample should be located almost exactly in the focal plane of the objective lens. Then, there are two overlapping beams above the objective lens (the downward-going excitation beam, and the upward-going fluorescence beam). By inserting, for example, a dichroic beam splitter, one of the beams is split off at an angel of 90°. This is possible because the fluorescence radiation has a longer wavelength than the excitation light. In many microscopes, the excitation beam is split off. In other words, an almost parallel excitation beam reaches a dichroic block, and is directed towards the objective lens. Fluorescence light, generated at the sample, passes straight through the dichroic block and reaches the imaging photodetector, or the observer's eye.

The method for calibrating a sample analyzer (disposable) according to the present invention can be summarized in the following seven steps:

Step 1

Measure fluorescence intensity values in cell-free locations within a calibration area of sufficient height.

Step 2

Extrapolate to the integrated fluorescence intensity, Ical, for a total calibration area of size, A, that could be expected under cell-free conditions.

Step 3

Measure fluorescence intensity values in cell-free locations within the single-cell area.

Step 4

Extrapolate to the integrated fluorescence intensity, Isca, for a total area of size, A, that could be expected under cell-free conditions.

Step 5

Determine an effective height, H, by using the equation $$H = \int_{-h/2}^{h/2} E(z) * D(z) \, dz \tag{4}$$

where $$E(z) = \left[ \frac{\sin(u_{ex}(z)/4)}{u_{ex}(z)/4} \right]^2 \tag{5}$$

where $$u_{ex}(z) = \frac{2 * \pi}{\lambda_{ex}} * (NA)^2 * z \tag{6}$$

where $$D(z) = \left[ \frac{\sin(u_{em}(z)/4)}{u_{em}(z)/4} \right]^2 \text{ and} \tag{7}$$

$$u_{em}(z) = \frac{2 * \pi}{\lambda_{em}} * (NA)^2 * z \tag{8}$$

and wherein NA is the numerical aperture of the microscope objective lens, $\lambda_{ex}$ is the excitation center-wavelength, $\lambda_{em}$ is the emission center-wavelength, and z is a position within the sample on an axis parallel to the microscope's imaging optics.

Step 6

Calculate a quantity K with $$K = \frac{I_{sca}}{I_{cal}} * H \tag{9}$$

Step 7

Determine an integration limit, d, that is a solution of the equation $$\int_{-d/2}^{d/2} E(z) * D(z) \, dz = K \tag{10}$$

whereby d is equal to the unknown sample height (which is equal to the cuvette height) in the single-cell area that is to be determined.

Steps 1 to 7 according to the present invention will now be discussed in more detail.

Step 1

Figure 1:
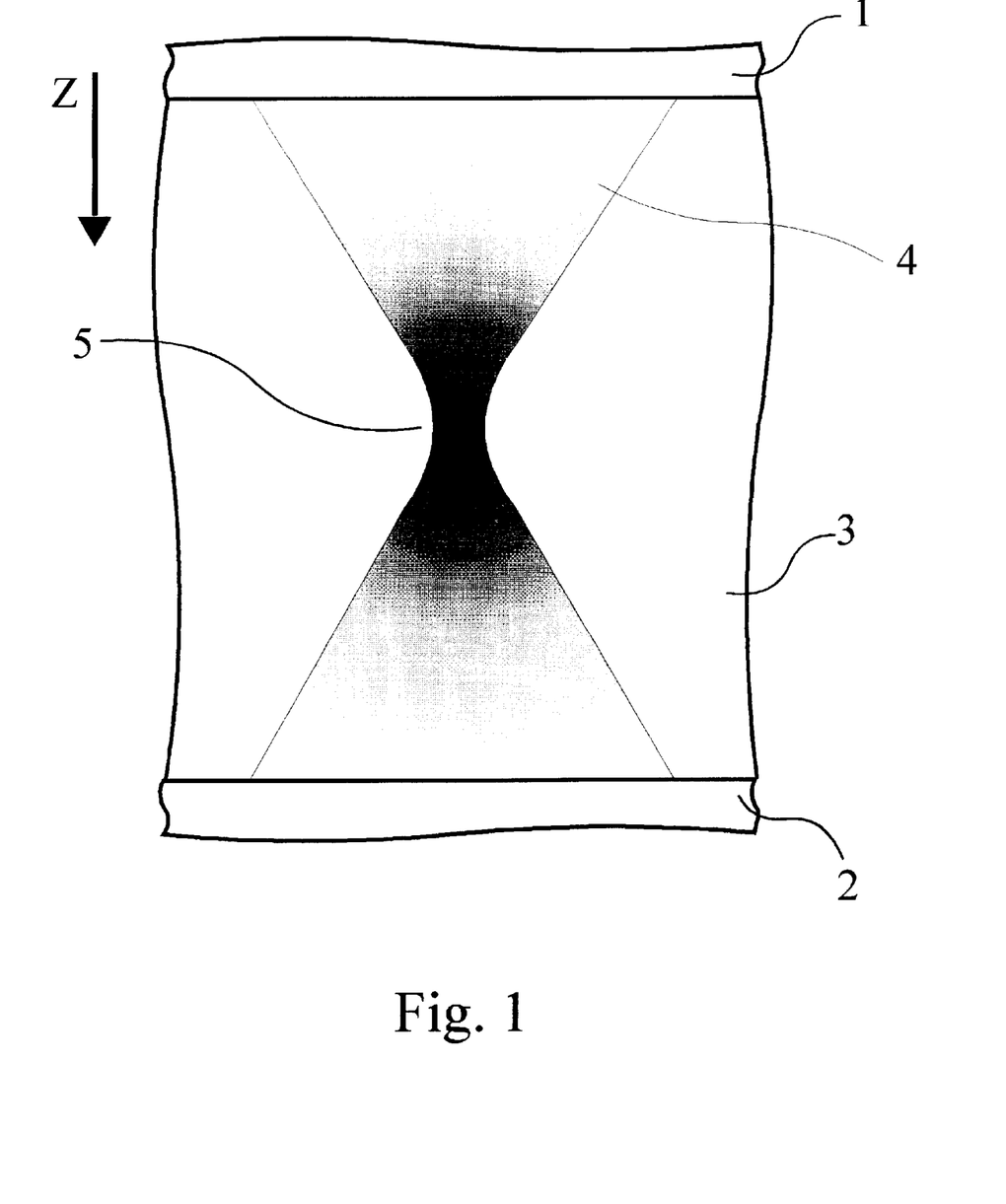
FIG. 1 shows schematically the double-cone of excitation light that is formed below the objective lens of a typical fluorescence microscope in EPI configuration.
Figure 2:
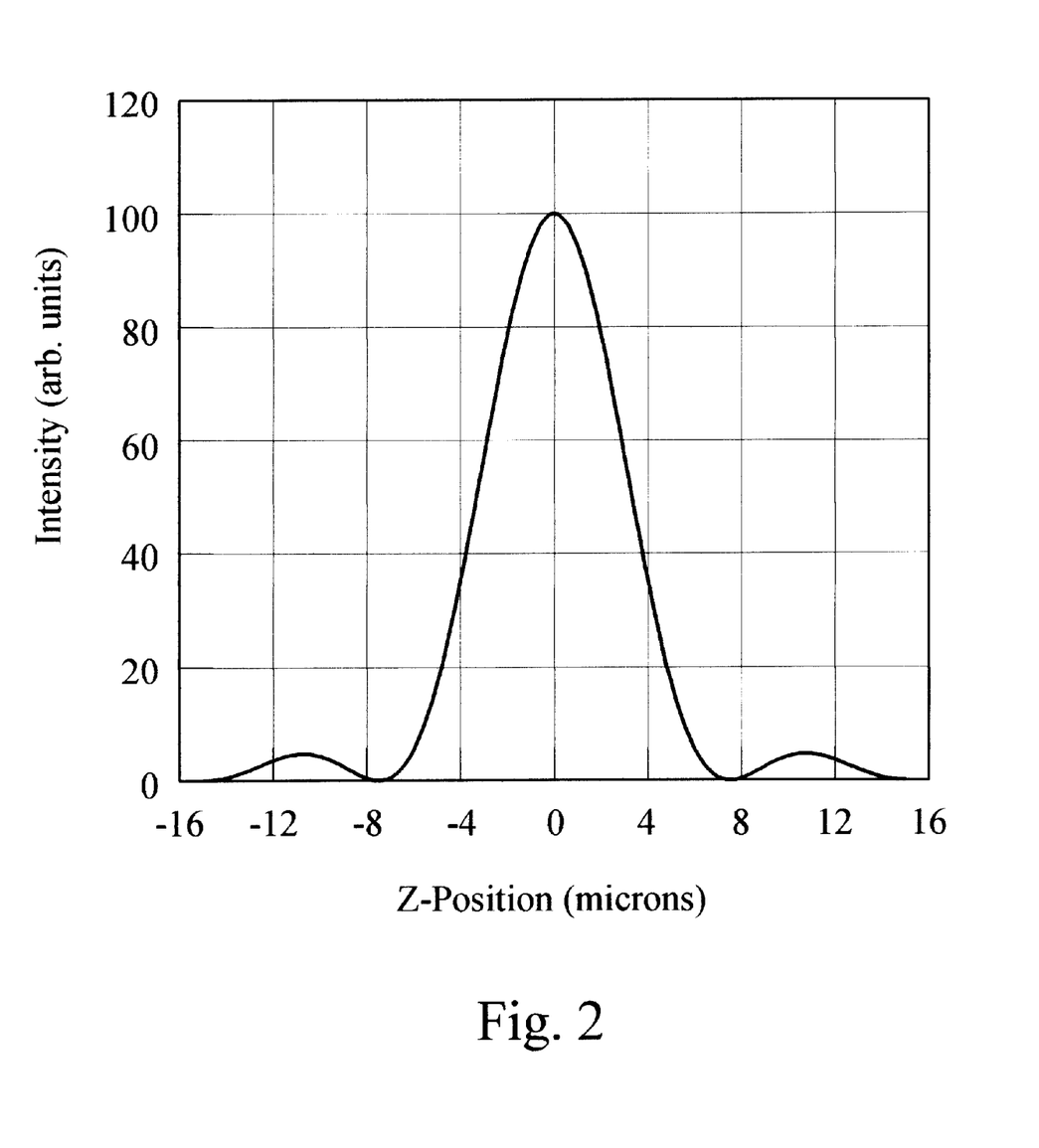
FIG. 2 illustrates the on-axis intensity within the liquid sample as a function of the Z-position, assuming an ideal lens with uniform illumination of the entrance pupil, a numerical aperture NA=0.4 and a wavelength λ=600 nm. The cuvette height is 32 microns (−16 . . . +16).

For illustration purposes, FIG. 1 shows schematically the double-cone of excitation light that is formed below the objective lens of a typical fluorescence microscope in EPI configuration. In FIG. 1, only the light within an optical cuvette is shown, whereby (1) is the upper window, (2) is the base plate, (3) is the liquid sample within the cuvette, (4) is the double-cone, and (5) is the beam waist. Obviously, maximum excitation intensity is obtained in the beam waist region. The plot in FIG. 2 illustrates the on-axis intensity within the liquid sample as a function of the Z-position. We have assumed an ideal lens with uniform illumination of the entrance pupil, a numerical aperture NA=0.4 and a wavelength λ=600 nm. The cuvette height in FIG. 2 is 32 microns (−16 . . . +16). The plot indicates that only part of the liquid volume is receiving maximum illumination intensity, and that within this part the intensity is not constant.

From FIG. 2, we can draw the following conclusion: If one would use a cuvette of variable height, then the measured fluorescence intensity would initially increase with increasing cuvette height. If, however, the cuvette height reaches values that are larger than the intensity distribution curve shown in FIG. 2, then the measured fluorescence intensity will reach an upper limit. In other words, any further increase in cuvette height will not cause a further increase in the measured fluorescence intensity.

Figure 3:
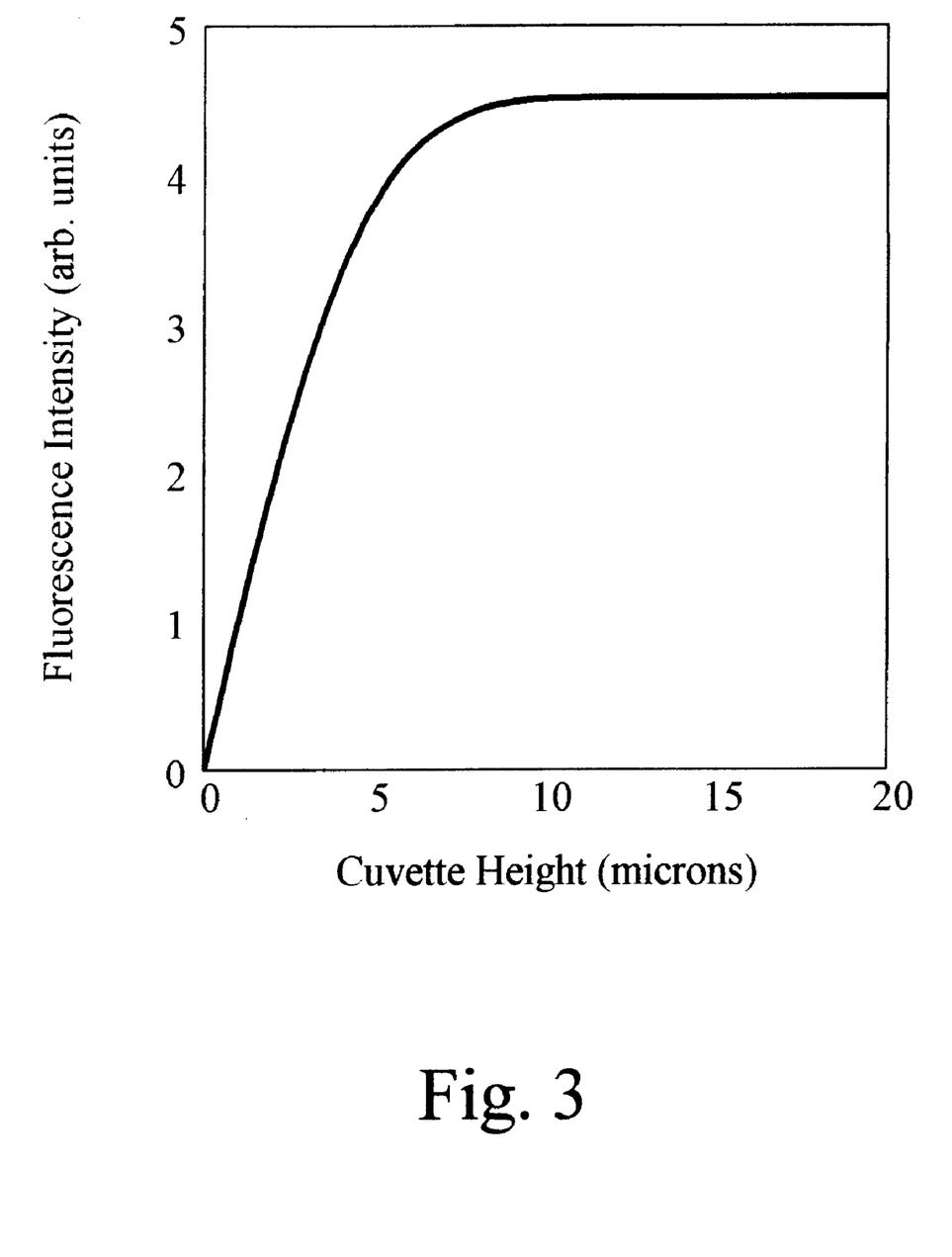
FIG. 3 shows the fluorescence intensity as a function of the cuvette height, assuming an objective lens of NA=0.4, an excitation center-wavelength $\lambda_{ex}$=500 nm, and an emission center-wavelength $\lambda_{em}$=600 nm.

FIG. 3 shows the fluorescence intensity as a function of the cuvette height, assuming an objective lens of NA=0.4, an excitation center-wavelength $\lambda_{ex}$=500 nm, and an emission center-wavelength $\lambda_{em}$=600 nm. Step 1 of the present invention is performed in a calibration area of "sufficient" height. By "sufficient" it is meant that the height is such that the upper fluorescence limit is measured.

It should be noted that the necessary minimum height that can be used for calibration according to the present invention depends on the numerical aperture, NA, of the objective lens, on the excitation wavelength range, $\Delta\lambda_{ex}$, and on the fluorescence emission wavelength range, $\Delta\lambda_{em}$. The emission wavelength range is involved here, since the plot shown in FIG. 2 does not only represent the excitation intensity, E(z), as a function of the Z-position within the cuvette, but also the Z-dependent photon collection efficiency, D(z), assuming a constant area, A, as "seen" by the microscope's imaging photodetector. In other words, for any specific experimental situation, characterized by NA, $\Delta\lambda_{ex}$, and $\Delta\lambda_{em}$, the minimum height that would be sufficient for calibrating the disposable can be determined mathematically. Instead of the wavelength ranges, also the center-wavelengths, $\lambda_{ex}$ and $\lambda_{em}$, respectively, can be used. As mentioned above, the plot in FIG. 3 applies to a numerical aperture of 0.4, an excitation center-wavelength of 500 nm, and an emission center-wavelength of 600 nm. The cuvette height that is "sufficient" for calibration is any height above 10 microns, because an increase beyond 10 microns would not result in increased fluorescence intensity.

Step 2

In Step 2, the total or integrated fluorescence intensity, Ical, for an area A, as seen by the microscope's imaging photodetector, is determined. This can be accomplished via the pixel histogram, or by using other common procedures known in the field of image processing. It is important that the integrated fluorescence intensity as determined in Steps 1 and 2 corresponds to a cell-free area.

Step 3

Step 3 is a repeat of step 1, but is performed in the "single-cell area" of the disposable, which is an area where RBC's are present in a monolayer and, preferably, separated from each other by some distance. The latter allows for easier image processing and improved precision in the RCV determination.

Step 4

Step 4 is the equivalent of Step 2, but repeated in the single-cell area.

Step 5

Equation (4) under Step 5 represents the calculation of the final integrated fluorescence intensity that can be expected from an area A as seen by the imaging photodetector. The intensity Ical would be given by the equation $$I_{cal} = \eta * I_0 * A * \int_{-h/2}^{+h/2} E(z) * D(z) dz \quad (11)$$

where η takes into account the fluorophore's quantum yield, the geometry, photodetector sensitivity, and electronic gain contributions. $I_0$ is the maximum excitation intensity, and A is again the area of photon collection as seen by the microscope's imaging photodetector. The quantity Ical can also be written as $$I_{cal} = C * H \quad (12)$$

with $$C = \eta * I_0 * A \quad (13)$$

and $$H = \int_{-h/2}^{+h/2} E(z) * D(z) dz \quad (14)$$

which is identical to equation (4). The quantity C in equations (12) and (13) can be considered as a calibration constant, but we will see later that it is canceled out by the procedure according to the present invention.

The quantity H in equation (14) can be considered as an "effective height" if one would assume a constant excitation intensity and constant photon collection efficiency along the Z-direction over a height H (see equation (12)). As mentioned above, the value of H can be calculated if one knows NA, $\lambda_{ex}$ and $\lambda_{em}$. Assuming NA=0.4, $\lambda_{ex}$=500 nm, and $\lambda_{em}$=600 nm, we obtain H=4.513 microns. It has to be emphasized that this calculation does not require any real fluorescence intensity measurement.

Similar to equation (11) for the calibration area, one can calculate the integrated fluorescence intensity that is expected from the single-cell area by $$I_{sca} = \eta * I_0 * A * \int_{-d/2}^{+d/2} E(z) * D(z) dz \quad (15)$$

where d represents the unknown cuvette height in the single-cell area that has to be determined. Dividing equation (15) by equation (11) and re-arranging somewhat results in $$\int_{-d/2}^{+d/2} E(z) * D(z) dz = H * \frac{I_{sca}}{I_{cal}}. \quad (16)$$

Equation (16) contains the crux of the present invention in the shortest possible form: determine that integration limit, d, which results in a value for the integral on the left side that is equal to the value of the expression on the right side, whereby the right side contains the combination of a theoretical value, H, and two experimentally determined integrated fluorescence intensities, Isca and Ical, respectively. As has been indicated above, by dividing equation (15) by equation (11), the calibration constant C from equation (13) that would contain the maximum excitation intensity and other experimental parameters, is canceled out.

Step 6

In Step 6 of the present invention, the quantity K which is identical to the right side of equation (16) is determined, based on the theoretical quantity H, and on the two experimentally determined integrated fluorescence intensities Isca and Ical. In an example, i.e. for NA=0.4, $\lambda_{ex}$=500 nm, $\lambda_{em}$=600 nm, and an assumed cuvette height of 3 micron in the single-cell area, one can calculate the expected values for Isca and Ical. Combining those with H=4.513 microns (as obtained above by solving equation (14)), results in K=2.705 microns. In the next step, this K-value is used to calculate the true height in the single-cell area.

Step 7

Figure 4:
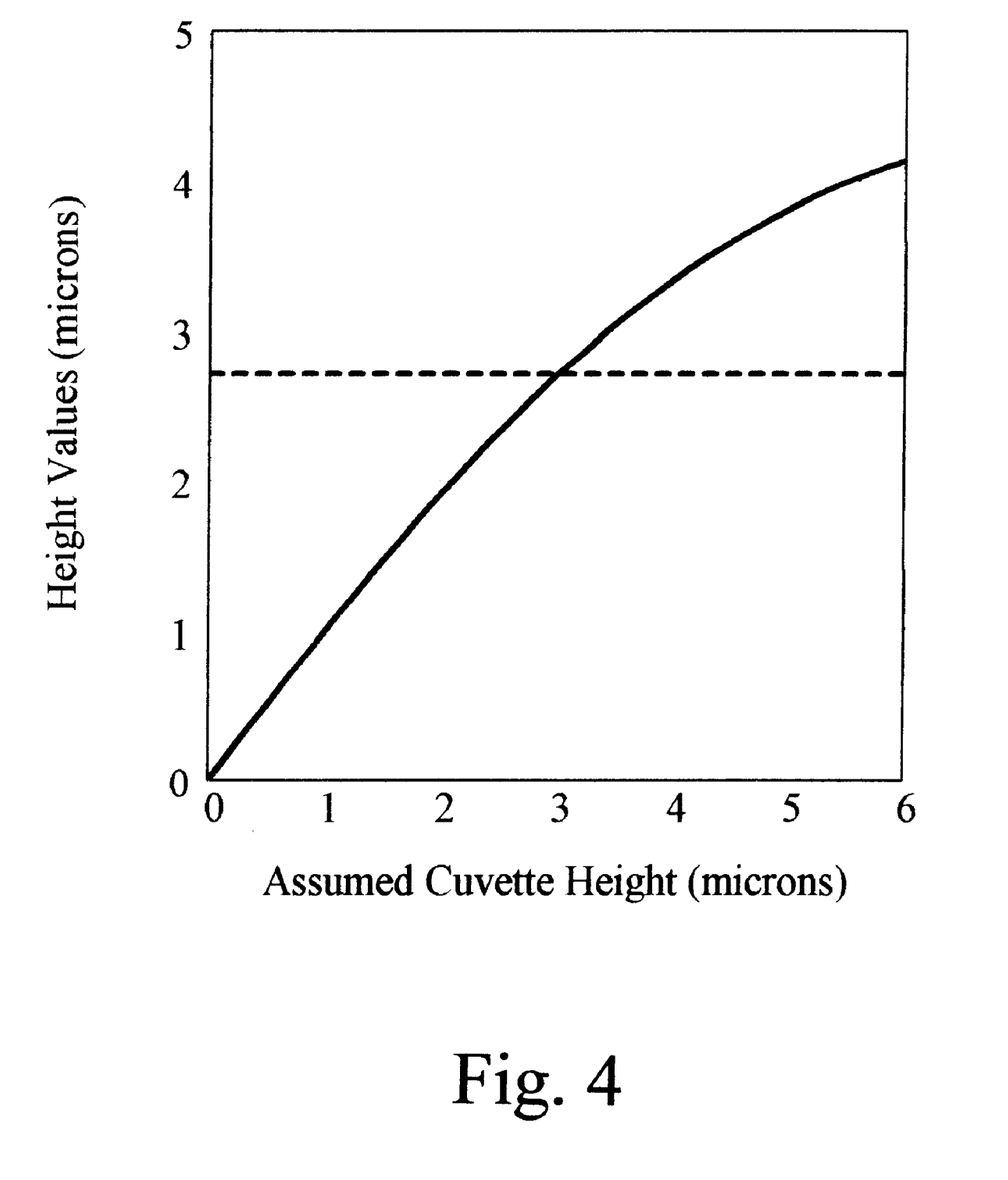
FIG. 4 shows the quantity K as a dashed line, and the integral of equation (10) as a function of the integration limit, d, assuming an objective lens of NA=0.4, an excitation center-wavelength $\lambda_x$=500 nm, an emission center-wavelength $\lambda_m$=600 nm, and a cuvette height of 3 micron in the single-cell area.

Step 7 is illustrated in FIG. 4, showing the K-value of 2.705 as a dashed line, and the integral from the left side of equation (16). With increasing cuvette height d, the value of the integral is also increasing. For d=3 microns, the value of the integral is identical to K=2.705, which corresponds, as expected, to the true cuvette height.

For a given experimental situation, characterized by NA, $\lambda_{ex}$, and $\lambda_{em}$, the integral in equation (16) can be determined for a monotonously increasing series of "assumed" cuvette heights. This data can then be stored in the form of a look-up table. Consequently, the method according to the present invention could be practiced by determining the quantity K, which takes into account the experimental values of Ical and Isca, and then looking up from the table to what particular cuvette height, d, the current H-value corresponds.

Figure 5:
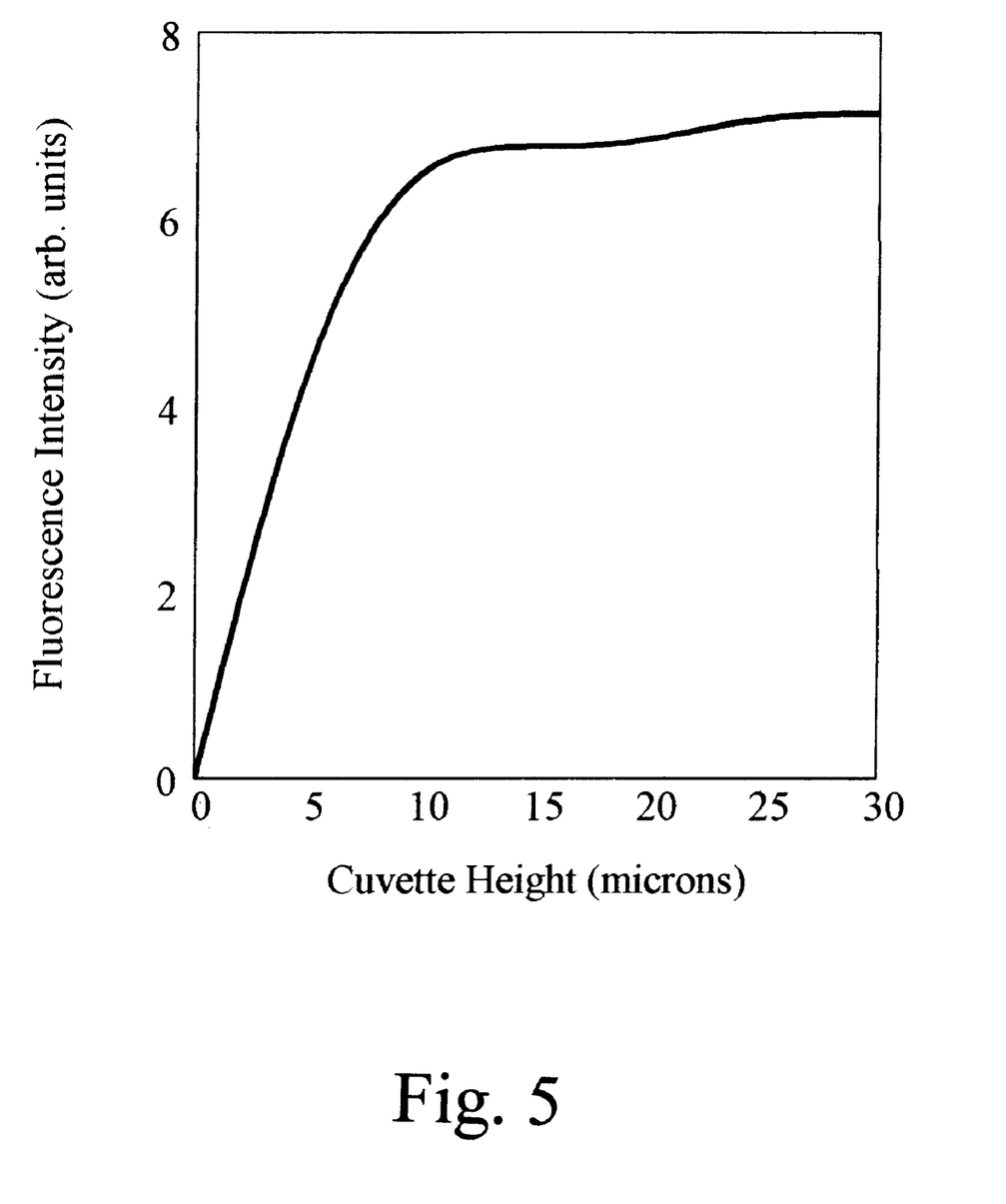
FIG. 5 corresponds to FIG. 3, but applies to a homogeneous excitation along the Z-axis.
Figure 6:
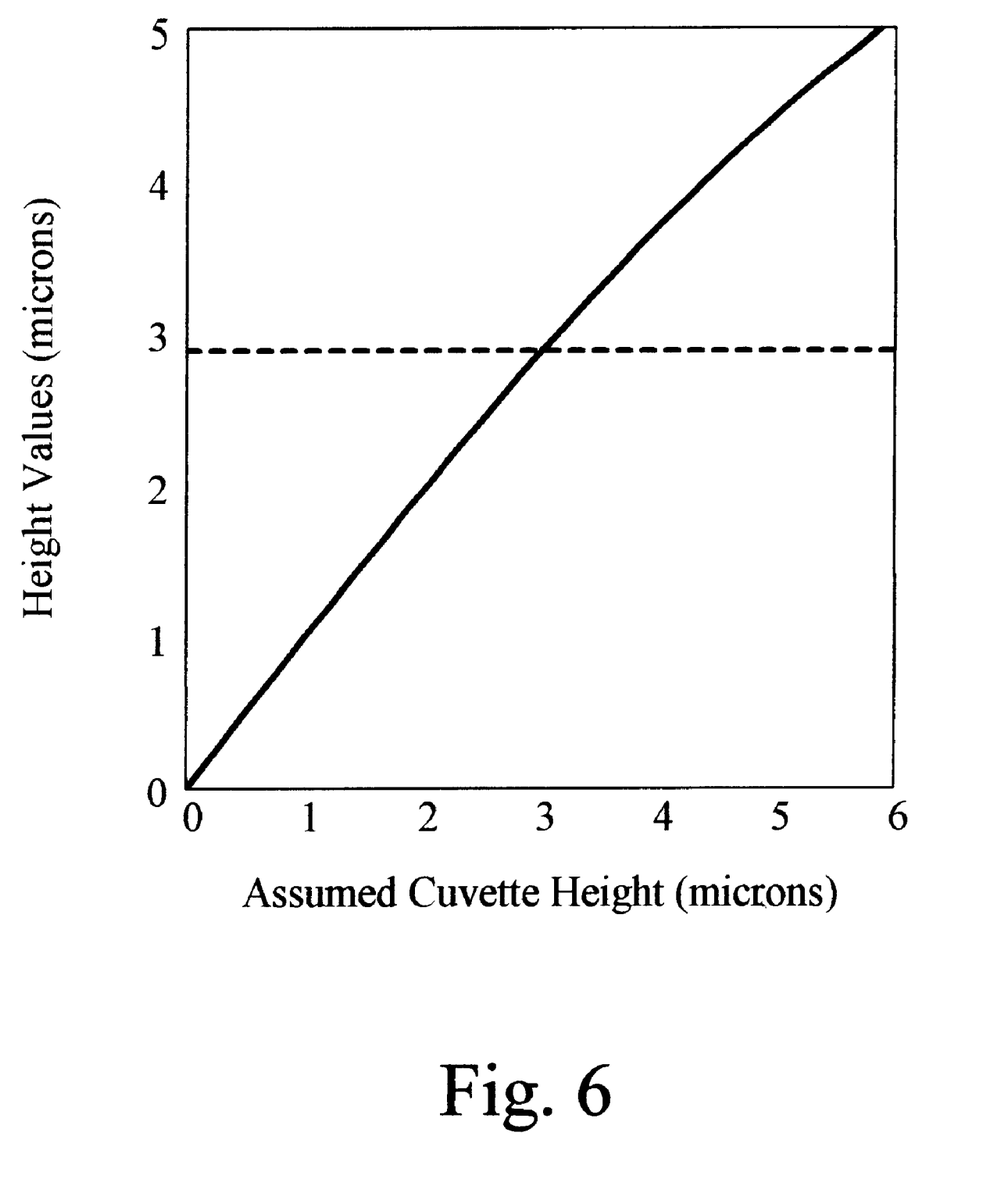
FIG. 6 corresponds to FIG. 4, but applies to a homogeneous excitation along the Z-axis.

So far, we have considered a fluorescence microscope where the sample is illuminated through the objective lens (EPI configuration). Using an EPI configuration has the advantage for common microscopic tasks that the excitation light is where one needs it. In common fluorescence microscopy, it is the restriction of the photon collection efficiency along the Z-axis, combined with the similarly restricted excitation along the Z-axis what allows one to obtain sharp images. For the current task of determining HCT and RCV, one could change over to a homogeneous illumination along the Z-axis, e.g. by illuminating the sample from the back-side or from the side without involving the objective lens in the illumination. In this context, it should be noted that the calibration method according to the present invention could also be applied in this case. Mathematically, one would insert a constant $E_0$=1 for E(z) in equations (5), (10), (11), (14), (15), and (16). Otherwise, the process steps would be the same. FIG. 5 illustrates that the calibration intensity, Ical, for the case of homogeneous illumination reaches a first plateau, and then exhibits an additional slight increase with increasing cuvette thickness. This means that in this case either a cuvette area with a thickness around 15 microns or a cuvette area with a thickness around 30 microns could be used. Again, there would be no need for knowing the exact thickness. FIG. 6 illustrates the final process step for homogeneous illumination.

In practice, it has been found that equations (5) to (8) do not always describe the actual on-axis distributions for illumination intensity and photon collection efficiency along the Z-axis. The reason for this is manifold. As an example, equations (5) to (8) do not account for minor artifacts such as light scattering within the sample, imperfections of the microscope optics, light refraction at the upper cuvette window, and the like. Consequently, the functions E(z) and D(z) in equation (4) may have to be determined experimentally. A separate determination of E(z) and D(z) is, however, not really required. It would be sufficient to take into account only the combined effect of E(Z) and D(z) by using a function F(z) with $$F(z)=E(z)*D(z) \qquad (17)$$

Furthermore, it would not even be necessary to determine the function F(z). Instead, and according to equations (4), (10), and (16), integrals over fluorescence intensity distributions as a function of varying cuvette height are required. Due to the fact that equations (4), (10), and (16) refer to the same illumination distribution and photon collection distribution, only one measurement series of measured fluorescence intensity as a function of cuvette height is required for establishing a relationship H(d), and for determining the "effective height" value according to equation (4) as H(h), where again h is a "sufficient" height. Both, H(d) and H(h) will contain a constant factor the value of which depends on the particular instrument that is used. However, because H(d) is identical to the left side of equation (10), and because H(h) is identical to H on the right side of equation (9), combining equations (9) and (10) shows that the constant factor is canceled out.

The calibration measurement described above can be performed, e.g., by using calibrated cuvettes of known height values, or by constructing a wedge-shaped cuvette from two stiff plates of a transparent material such as glass. If a spacer of known height is used at the thick end of the wedge-shaped cuvette, well-defined height values can be established by selecting appropriate locations within the wedge. Once the integrals H(d) and H(h) have been determined for a given fluorescence microscope, the present invention can be practised as described above.

As can be seen from FIG. 3, the integral in equations (10) and (16) shows an almost linear behavior for very small cuvette height values below 5 microns, i.e. for height values used in the single-cell area. Using the approximation $$\int_{-d/2}^{d/2} E(z)*D(z)\,dz = P*d \qquad (18)$$

with P being a constant factor, equation (16) can be re-written as $$P*d = H*\frac{I_{sca}}{I_{cal}}. \qquad (19)$$

The quantity H in equation (19), as defined by equation (4), depends on such parameters as NA, $\lambda_{ex}$, $\lambda_{em}$, and others. For a given fluorescence microscope configuration, it will be a constant. Therefore, equation (19) can be written as $$d = G*\frac{I_{sca}}{I_{cal}}. \qquad (20)$$

with G=H/P being another constant that has to be determined only once for a particular microscope configuration.

Equation (20) describes the simplest way to practice the present invention:

After a one-time calibration to obtain the value of a constant G, the fluorescence intensity, Isca, re-emerging from an area of size A in a cell-free location in the single-cell area is determined, then the fluorescence intensity, Ical, re-emerging from an area of size A in a cell-free location in a region of "sufficient" height is determined, and, finally, the cuvette height, d, in that location within the single-cell area is calculated via the equation d=G*(Isca/Ical). The one-time calibration can be performed by utilizing a chamber of small but known height d' and determining a first calibration constant as P=H(d')/d'. Then, a second measurement is performed at a "sufficient" height, h, which provides the quantity H(h). The final calibration constant, G, is then obtained as G=H(h)/P.

The present invention is based on the surprising fact that a height value in the single-cell area can be determined by measuring a fluorescence intensity in that area, and by measuring another fluorescence intensity in a second area, whereby the exact height in that second area has not to be known. The only requirement is that the height in the second area is "sufficient", whereby "sufficient" means that for the given microscope configuration the fluorescence intensity becomes independent of the height. An estimate of a sufficient height can be performed by plotting equation (10) as a function of d (see FIG. 3), and selecting a height where the fluorescence intensity has reached the plateau. It is important to note that the actual height value is not required to practise the invention.

As can be seen from equations (16) and (20), the method according to the present invention is using a ratio of two measured fluorescence intensities, namely Isca and Ical. Since both intensities are proportional to such factors as excitation intensity, transmission of the optical system, filter transmission, CCD detector sensitivity, and others, any changes or drift artifacts in all of those parameters are canceled out. Therefore, the method according to the present invention produces accurate results.

It would of course still be within the spirit of the present invention to use the disclosed calibration method not only for blood analyzers, but also for analyzers that analyze other liquid samples that may or may not contain any particles in suspension. In this case, particle-free locations in other samples would correspond to cell-free locations in a blood sample. Accordingly, cuvette areas of low height, where particles exist isolated from each other (single-particle areas) would correspond to single-cell areas in a blood sample. It would also be within the spirit of the invention to apply the calibration method not only to microscopes but also to other optical scanning instruments.

In summary, the present invention is directed to a calibration method for sample analyzers, and preferably sample analyzer disposables, that works perfectly with the typical non-homogenous illumination and non-homogenous photon collection efficiency along the Z-axis, and does not require molded high-precision calibration features within the disposable.

I claim:

1. A method for calibrating the sample height of a sample in a chamber of a sample analyzer held within an optical scanning instrument, said method comprising:

a) providing said chamber for receiving a sample, in said sample analyzer;
   b) depositing a sample into said chamber wherein said sample contains a fluorescent dye;
   c) illuminating said sample with excitation light;
   d) scanning the sample with said instrument to detect the fluorescence from said sample;
   e) measuring fluorescence intensity values in particle-free locations within a calibration area of such height, h, that the measured fluorescence intensity is independent of the height value;
   f) extrapolating to the integrated fluorescence intensity, Ical, for a total calibration area of size, A;
   g) measuring fluorescence intensity values in particle-free locations within a single-particle area;
   h) extrapolating to the integrated fluorescence intensity, Isca, for a total area of size, A;
   i) determining an effective height, H, in the calibration area by using the equation $$H = \int_{-h/2}^{h/2} E(z) * D(z) dz$$

where $$E(z) = \left[ \frac{\sin(u_{ex}(z)/4)}{u_{ex}(z)/4} \right]^2$$

where $$u_{ex}(z) = \frac{2*\pi}{\lambda_{ex}} * (NA)^2 * z$$

where $$D(z) = \left[ \frac{\sin(u_{em}(z)/4)}{u_{em}(z)/4} \right]^2$$

where $$u_{ex}(z) = \frac{2*\pi}{\lambda_{ex}} * (NA)^2 * z$$

and wherein NA is the numerical aperture of the scanning instrument's objective lens, $\lambda_{ex}$ is the excitation center-wavelength, $\lambda_{em}$ is the emission center-wavelength, and z is a position within the sample on an axis parallel to the scanning instrument's imaging optics;

j) calculating a quantity K where $$K = \frac{I_{sca}}{I_{cal}} * H;$$

k) determining an integration limit, d, that is a solution of the equation:

$$\int_{-d/2}^{d/2} E(z) * D(z) dz = K$$

whereby d is equal to the unknown sample height in the single-cell area that is to be determined; and l) obtaining the calibrated sample height.

2. The method of claim 1 wherein said sample is blood.

3. The method of claim 1 wherein said sample is whole blood.

4. The method of claim 1 wherein said particles are blood cells.

5. The method of claim 1 wherein said chamber is an optical cuvette.

6. The method of claim 1 wherein said chamber is a disposable chamber.

7. The method of claim 1 wherein said optical scanning instrument is a microscope.

8. The method of claim 1 wherein said optical scanning instrument is a fluorescence microscope.

9. The method of claim 1 wherein said optical scanning instrument is a fluorescence microscope in EPI configuration.

10. The method of claim 1 wherein said optical scanning instrument is a confocal microscope.

11. A method for calibrating the sample height of a sample in a chamber of a sample analyzer held within an optical scanning instrument, said method comprising:
  a) providing said chamber for receiving a sample, in said sample analyzer;
  b) depositing a sample into said chamber wherein said sample contains a fluorescent dye;
  c) illuminating said sample with excitation light;
  d) scanning the sample with said instrument to detect the fluorescence from said sample;
  e) measuring fluorescence intensity values in particle-free locations within a calibration area of such height, h, that the measured fluorescence intensity is independent of the height value;
  f) extrapolating to the integrated fluorescence intensity, Ical, for a total calibration area of size, A;
  g) measuring fluorescence intensity values in particle-free locations within a single-particle area;
  h) extrapolating to the integrated fluorescence intensity, Isca, for a total area of size, A;
  i) measuring, on the same instrument, a height-dependent fluorescence intensity H(d) for calibration by using a set of chambers of variable but known height, d;
  j) measuring a fluorescence intensity H(h);
  k) determining the one d-value that is a solution of the equation:

$$H(d) = \frac{I_{sca}}{I_{cal}} * H(h)$$

whereby d is equal to the unknown sample height in the single-cell area that is to be determined; and
  m) obtaining the calibrated sample height.

12. The method of claim 11 whereby the data for the height-dependent fluorescence intensity H(d), and for the fluorescence intensity H(h) according to steps (i) and (j) are obtained from a prior calibration.

13. The method of claim 11 wherein said sample is blood.

14. The method of claim 11 wherein said sample is whole blood.

15. The method of claim 11 wherein said particles are blood cells.

16. The method of claim 11 wherein said chamber is an optical cuvette.

17. The method of claim 11 wherein said chamber is a disposable chamber.

18. The method of claim 11 wherein said optical scanning instrument is a microscope.

19. The method of claim 11 wherein said optical scanning instrument is a fluorescence microscope.

20. The method of claim 11 wherein said optical scanning instrument is a fluorescence microscope in EPI configuration.

21. The method of claim 11 wherein said optical scanning instrument is a confocal microscope.

22. A method for calibrating the sample height of a sample in a chamber of a sample analyzer held within an optical scanning instrument, said method comprising:
  a) providing said chamber for receiving a sample, in said sample analyzer;
  b) depositing a sample into said chamber wherein said sample contains a fluorescent dye;
  c) illuminating said sample with excitation light;
  d) scanning the sample with said instrument to detect the fluorescence from said sample;
  e) measuring fluorescence intensity values in particle-free locations within a calibration area of such height, h, that the measured fluorescence intensity is independent of the height value;
  f) extrapolating to the integrated fluorescence intensity, Ical, for a total calibration area of size, A;
  g) measuring fluorescence intensity values in particle-free locations within a single-particle area;
  h) extrapolating to the integrated fluorescence intensity, Isca, for a total area of size, A;
  i) measuring, on the same instrument, a fluorescence intensity H(d')=P*d' for calibration by using a chamber of small but known height, d';
  j) determining a first calibration constant P=H(d')/d';
  k) measuring a fluorescence intensity H(h);
  l) calculating a final calibration constant G=H(h)/P;
  m) determining the one d-value that is a solution of the equation:

$$d = G * \frac{I_{sca}}{I_{cal}}$$

whereby d is equal to the unknown sample height in the single-cell area that is to be determined;
  n) obtaining the calibrated sample height.

23. The method of claim 22 whereby the value for the constant G according to steps (i) to (l) is obtained from a prior calibration.

24. The method of claim 22 wherein said sample is blood.

25. The method of claim 22 wherein said sample is whole blood.

26. The method of claim 22 wherein said particles are blood cells.

27. The method of claim 22 wherein said chamber is an optical cuvette.

28. The method of claim 22 wherein said chamber is a disposable chamber.

29. The method of claim 22 wherein said optical scanning instrument is a microscope.

30. The method of claim 22 wherein said optical scanning instrument is a fluorescence microscope.

31. The method of claim 22 wherein said optical scanning instrument is a fluorescence microscope in EPI configuration.

32. The method of claim 22 wherein said optical scanning instrument is a confocal microscope.

33. A method for calibrating the sample height of a sample in a first chamber of a sample analyzer held within an optical scanning instrument, said method comprising:
  a) providing said first chamber for receiving a sample, in said sample analyzer;
  b) depositing a sample into said chamber wherein said sample contains a fluorescent dye;
  c) illuminating said sample with excitation light;
  d) scanning the sample with said instrument to detect the fluorescence from said sample;
  e) measuring fluorescence intensity values in particle-free locations within a calibration area of such height that the measured fluorescence intensity is independent of the height value;
  f) measuring fluorescence intensity values in particle-free locations within a single-particle area;
  g) measuring, on the same instrument, a fluorescence intensity for calibration by using a second chamber of small but known height, said second chamber being filled with a fluorescent liquid;

h) measuring, on the same instrument, a fluorescence intensity for calibration by using a third chamber of such height that the measured fluorescence intensity is independent of the height value, said third chamber being also filled with said fluorescent liquid;

i) calculating a calibration constant;

j) determining the sample height within said single-particle area in said first chamber from the two measured fluorescence intensity values and said calibration constant;

k) obtaining the calibrated sample height.

34. The method of claim 33 whereby the value for the calibration constant is obtained from a prior calibration.

35. The method of claim 33 wherein said sample is blood.

36. The method of claim 33 wherein said sample is whole blood.

37. The method of claim 33 wherein said particles are blood cells.

38. The method of claim 33 wherein said chamber is an optical cuvette.

39. The method of claim 33 wherein said chamber is a disposable chamber.

40. The method of claim 33 wherein said optical scanning instrument is a microscope.

41. The method of claim 33 wherein said optical scanning instrument is a fluorescence microscope.

42. The method of claim 33 wherein said optical scanning instrument is a fluorescence microscope in EPI configuration.

43. The method of claim 33 wherein said optical scanning instrument is a confocal microscope.

* * * * *